(12) United States Patent
Merchant, Jr.

(10) Patent No.: US 8,214,052 B2
(45) Date of Patent: Jul. 3, 2012

(54) METHOD OF IMPROVED VEIN CLOSURE

(76) Inventor: Robert F. Merchant, Jr., Reno, NV (US)

( * ) Notice: Subject to any disclaimer, the term of this patent is extended or adjusted under 35 U.S.C. 154(b) by 534 days.

(21) Appl. No.: 12/359,970

(22) Filed: Jan. 26, 2009

(65) Prior Publication Data
US 2009/0192544 A1 Jul. 30, 2009

Related U.S. Application Data

(60) Provisional application No. 61/023,404, filed on Jan. 24, 2008.

(51) Int. Cl.
A61F 2/00 (2006.01)

(52) U.S. Cl. ........................................ 607/101

(58) Field of Classification Search .................. 604/22; 607/96–107, 115–117; 600/27–52
See application file for complete search history.

(56) References Cited

U.S. PATENT DOCUMENTS

| | | | | |
|---|---|---|---|---|
| 3,595,239 | A | * | 7/1971 | Petersen .................. 606/45 |
| 5,437,664 | A | * | 8/1995 | Cohen et al. ............. 606/42 |
| 6,565,521 | B1 | * | 5/2003 | Silberg .................... 601/2 |
| 7,163,533 | B2 | * | 1/2007 | Hobbs et al. ............. 606/11 |
| 2008/0021527 | A1 | * | 1/2008 | Hennings et al. ........ 607/89 |

OTHER PUBLICATIONS

The VNUS Closure Procedure—A Solution to Leg Pain and Varicose Veins, VNUS Medical Technologies, Inc., San Jose, California, www.vnus.com, 2007.
The VNUS Closure Procedure, VNUS Medical Technologies, Inc., San Jose, California, www.vnus.com, 2007.
T.M. Proebstle, M.D., et al, "Treatment of Incompetent Great Saphenous Vein by Endovenous Radiofrequency Powered Segmental Thermal Ablation: First Clinical Experience," Journal of Vascular Surgery, pp. 151-156.e1 (Jan. 2008).

* cited by examiner

Primary Examiner — Manuel Mendez
(74) Attorney, Agent, or Firm — Holland & Hart LLP

(57) ABSTRACT

There are disclosed methods of vein closure. In an embodiment, a method includes elevating a leg of a patient during a vein closure procedure so as to effect substantial emptying of the vein. The method also includes applying radio-frequency energy to a vein within the leg of the patient to cause the vein closure. In another embodiment, a method includes elevating a leg of a patient during a vein closure procedure within a range of about 30 degrees to about 45 degrees from a horizontal position. The method also includes applying radio-frequency energy to a vein within the leg of the patient. In one embodiment, a method includes elevating a leg, and emptying of a segment of the vein prior to applying radio-frequency energy. In another embodiment, the method includes elevating a leg of a patient, and applying energy to a vein. Other embodiments are also disclosed.

22 Claims, 4 Drawing Sheets

METHOD OF IMPROVED VEIN CLOSURE

REFERENCE TO PENDING PRIOR PATENT APPLICATION

This application claims the benefit under 35 U.S.C. 119 (e) of U.S. Provisional Patent Application No. 61/023,404, filed Jan. 24, 2008 by Robert F. Merchant for "Method of Improved Vein Closure," which patent application is hereby incorporated herein by reference.

BACKGROUND

Investigations into the therapeutic use of radiofrequency (RF) energy in man occurred as early as the late 19th and early 20th centuries. Technological advances increased interest in RF applications. Because, of its precise control of energy delivery and reliability, RF energy has been used for decades in neurosurgical techniques. (Liu J K, Apfelbaum R I. Treatment of trigeminal neuralgia. *Neurosurg Clint N Amer.* 2004; 15:319-34.). By the 1980s cardiac arrhythmias were being treated with RF devices. (Filingeri V, Gravante G, Cassisa D. Physics of radiofrequency in proctology. *Eur Rev Med Pharmacol Sci.* 2005;9:349-54.) Usage expanded to include treatment of various malignancies, including hepatic, renal, musculoskeletal, breast, lymph, spleen, pulmonary (Brown D B. Concepts, considerations, and concerns on the cutting edge of radiofrequency ablation. *J Vasc Interv Radiol.* 2005;16:597-613, and Gillams A R. The use of, radiofrequency in cancer. *Br J Cancer.* 2005;92:1825-9), as well as ophthalmologic maladies, gastric reflux, sleep apnea and aesthetic dermatological conditions. (Berjano E J. Theoretical modeling for radiofrequency ablation: state-of-the-art and challenges for the future. *Biomed Eng Online.* Apr. 18, 2006;5:24, and Sadick N, Sorhaindo L. The radiofrequency frontier: a review of radiofrequency and combined radiofrequency pulsed-light technology in aesthetic medicine. *Facial Plast Surg.* 2005;21: 131-8.) Berjano reported that the number of scientific papers published on the topic of therapeutic RF energy use increased from 19 in 1990 to 825 in 2005. (Berjano E J. Theoretical modeling for radiofrequency ablation: state-of-the-art and challenges for the future. *Biomed Eng Online.* Apr. 18, 2006; 5:24.) As a less invasive alternative to vein stripping for elimination of saphenous vein reflux, the percutaneous catheter-based radiofrequency Closure® procedure (VNUS Medical Technologies, San Jose, Calif.) was introduced in Europe in 1998, and in the U.S. in 1999.

Following initial experience with the Closure procedure and early technique modifications, it became clear that reflux at the saphenofemoral junction (SFJ) could be eliminated by obliteration of the great saphenous vein in the thigh without resorting to dissection and ligation of all contributing branches near the saphenofemoral junction, (Chandler J G, Pichot O, Sessa C, et al. Defining the role of extended saphenofemoral junction ligation: A prospective comparative study. *J Vasc Surg.* 2000;32:941-53, and Chandler J G, Pichot O, Sessa C, et al. Treatment of primary venous insufficiency by endovenous saphenous vein obliteration. *Vasc Surg.* 2000; 34:201-14) thus eliminating the need for a groin incision and potential for minor and even major complications that can occur following traditional ligation and stripping procedures, and leaving intact venous return and lymphatic drainage from the abdominal wall and lower extremity. The validity of this strategy has been borne out by several published mid-term reports. (Nicolini P; Closure Group. Treatment of primary varicose veins by endovenous obliteration with the VNUS closure system: results of a prospective multicentre study. *Eur J Vasc Endovasc Surg.* 2005;29:433-9; Merchant R F, Pichot O, Myers K A. Four-year follow-up on endovascular radiofrequency obliteration of great saphenous reflux. *Dermatol Surg.* 2005;31:129-34; Pichot O, Kabnick L S, Creton D, et al. Duplex ultrasound scan findings two years after great saphenous vein radiofrequency endovenous obliteration. *J Vasc Surg.* 2004;39:189-95; and Lurie F, Creton D, Eklof B, et al. Prospective randomised study of endovenous radiofrequency obliteration (closure) versus ligation and vein stripping (EVOLVeS): two-year follow-up. *Eur J Vasc Endovasc Surg.* 2005;29:67-73.) Pichot (Pichot O, Kabnick L S, Creton D, et al. Duplex ultrasound scan findings two years after great saphenous vein radiofrequency endovenous obliteration. *J Vasc Surg.* 2004;39:189-95) coordinated an extensive two year follow-up ultrasound evaluation study from five VNUS, Registry centers. The results showed that 58/63 (92.1%) treated GSV segments remained free of reflux. Junctional tributary reflux was seen in 7/63 (11.1%) limbs, four of which were associated with the SFJ as the sole source of reflux. Neovascularization was not observed in any treated limbs. More recently, Closure equipment innovations and technique modifications have contributed to reduced procedure times while maintaining efficacy and low rates of complications.

For some closure procedures, such as the VNUS Closure procedure, a catheter with a radio-frequency (RF) heating coil may be used to close a vein within a leg of a patient. During the procedure, the heating coil must be drawn down the leg and compression must be maintained over the length of the heating coil as the patient is supported supine on a table.

Generally, it is very cumbersome to maintain this pressure and an additional technician may be necessary to maintain such pressure. The heat from the coil must also be applied for a given amount of time. This timing is generally 20 seconds for each 7 cm section of coil, with the first segment heated twice, and then periodically repositioned with pressure being regulated. This treatment may take 20 minutes to complete. Results from this procedure may be less than optimal due to the cumbersome and complex pressure maintenance and timing involved.

SUMMARY OF THE INVENTION

In an embodiment, there is provided a method of vein closure, the method comprising elevating a leg of a patient during a vein closure procedure so as to effect substantial emptying of the vein; and applying radio-frequency (RF) energy to a vein within the leg of the patient to cause the vein closure, wherein the radio-frequency (RF) energy is applied with a heating coil of a catheter within the vein during the procedure.

In another embodiment, there is provided a method of vein closure, the method comprising elevating a leg of a patient during a vein closure procedure within a range of about 30 degrees to about 45 degrees from a horizontal position; and applying radio-frequency (RF) energy to a vein within the leg of the patient to cause the vein closure with the leg of the patient elevated within the range of about 30 degrees to about 45 degrees.

In yet another embodiment, there is provided a method of vein closure, the method comprising elevating a leg of a patient during a vein closure procedure; emptying of a segment the vein prior to applying radio-frequency (RF) energy to the segment of the vein; and applying the radio-frequency (RF) energy to the vein within the leg of the patient to cause the vein closure.

In yet another embodiment, there is provided a method of vein closure, the method comprising elevating a leg of a patient during a vein closure procedure so as to effect substantial emptying of the vein; and applying energy to a vein within the leg of the patient to cause the vein closure, wherein the energy is applied to the vein during the procedure.

Other embodiments are also disclosed.

BRIEF DESCRIPTION OF THE DRAWINGS

Illustrative embodiments of the invention are illustrated in the drawings, in which.

DETAILED DESCRIPTION

Figure 1:
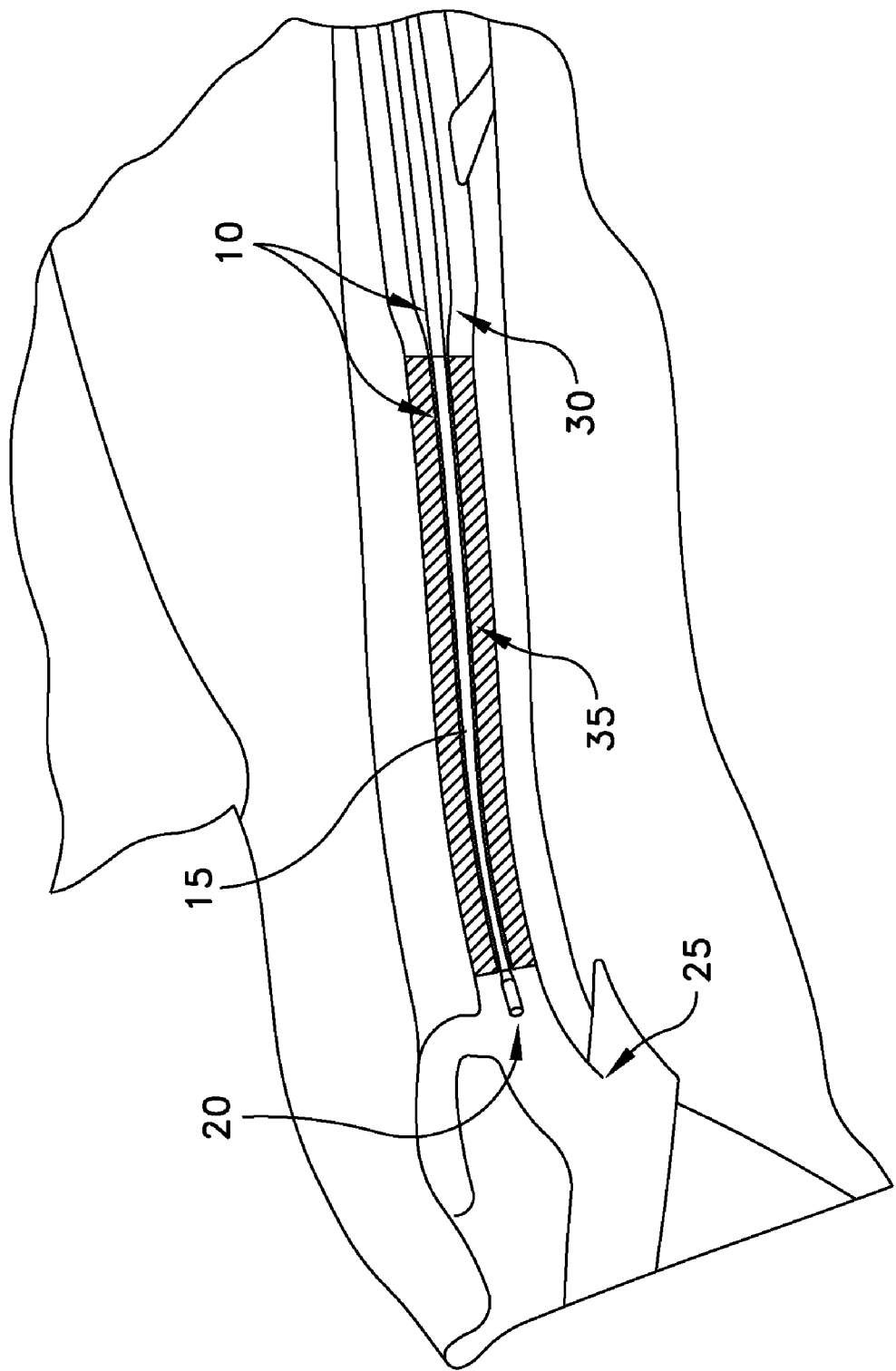
FIG. 1 illustrates a distal section of a ClosureFAST catheter, which contains a 7 cm long heating element, is depicted heating the great saphenous vein (GSV) in a segment starting approximately 2 cm below the saphenofemoral junction (SFJ).

In an embodiment, there is disclosed a method of positioning a patient for a VNUS Closure procedure to close a diseased vein using radio-frequency (RF) energy to heat the vein wall. In other embodiments, a vein may be closed using other types of heating, which may include, but are not limited to, endoluminal heating with a laser or another light source, steam, other electromagnetic energy. Vein closure is referred to herein with respect to radio-frequency (RF) energy, but may be practiced with one or more of these alternatives. The method may include positioning the patient with his or her legs at an angle of about 45°. Light pressure may be applied to the catheter heating coil during initial energy delivery. Sequential indexed heating may be continued as directed by the usual protocol, but compression is not applied unless energy and temperature have not reached a target range.

In one embodiment, the method may include elevating a patient's legs so as to empty the vein. Generally, the method includes positioning the patient's at an angle relative to the torso. In an exemplary embodiment, the angle of the legs relative to the torso is about 45°. In various embodiments, the leg undergoing the VNUS Closure procedure may be elevated independently during the procedure. The legs may be positioned at various angles that provide elevation so as to cause vein emptying.

For a successful vein closure procedure, the vessel wall must be in contact with the heating tip or coil. Compression of the vein may provide mixed results in as much as the catheter may remain either partially or completely bathed in blood. Vein emptying caused by elevation of the legs relative to the torso of the patient allow venous return of the blood within the vessel. This emptying of the vein provides good contact of the heating tip with the vessel wall, which in turn provides improved vein closure.

Other advantages are provided in addition to the improved vein closure described above. For example, the entire vein closure procedure using the elevated leg position allows a more smooth movement of the heating tip of the catheter. The total time of the procedure may be reduced from about 20 minutes to about 1.5 minutes (generally less than 2 minutes) to treat an entire thigh of the patient. Another advantage is that the catheter of the VNUS Closure procedure does not need to be redesigned. To provide better vein closure, other designs and modifications have been contemplated which may have increased the length of time for the procedure.

In one embodiment, the legs are elevated by using a table with a support for elevating the legs. Optionally, the table may be configured to include an adjustable back support portion. This back support portion may be positioned upwardly from a horizontal position to an angle of about 45°. The table may also include a tilt component. With this tilt component, the portion supporting the patient's back may be adjusted together with a leg supporting portion so as to comfortably adjust the patient's legs to an angle of about 45°. The position of the catheter tip may be checked to determine no migration during position change of the patient.

Technique

Unlike earlier attempts to obliterate the saphenous vein by diathermy, the endovenous Closure procedure uses radiofrequency energy to heat the vein wall. The ClosurePLUS™ catheter employs intralumenally positioned bipolar electrodes located at the tip in contact with the vein wall. Electrical current flowing between the electrodes through the vein wall tissue generates heat by a phenomenon called "resistive heating". The new ClosureFAST™ catheter (illustrated in FIG. 1) utilizes radiofrequency energy to heat a 7 cm long element near the tip resulting in direct conduction to the vein wall.

Figure 2:
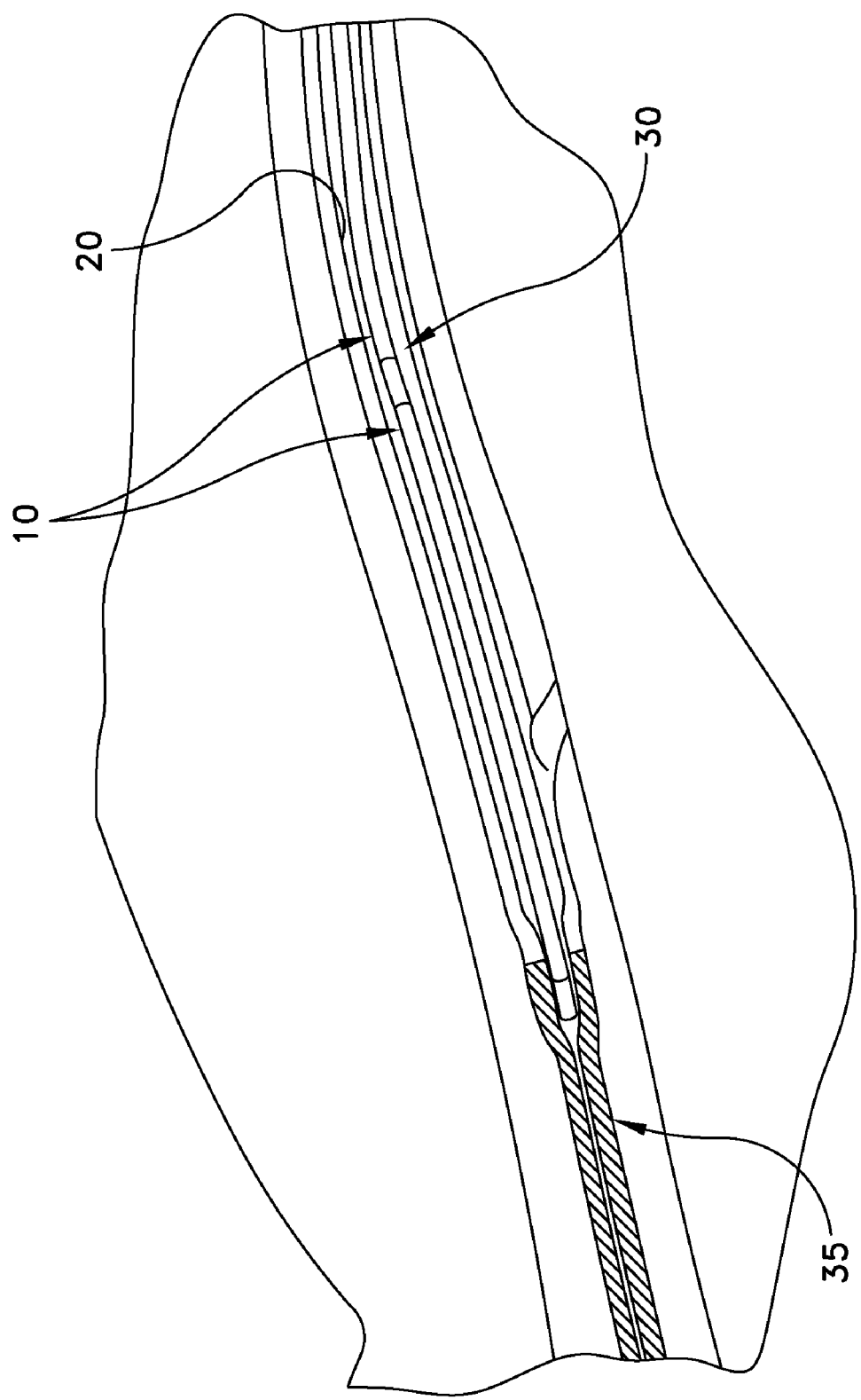
FIG. 2 illustrates a catheter prior to heating a segment of the vein at a heating element, with a closed segment of the vein to the left of the segment to be heated by heating element.
Figure 3:
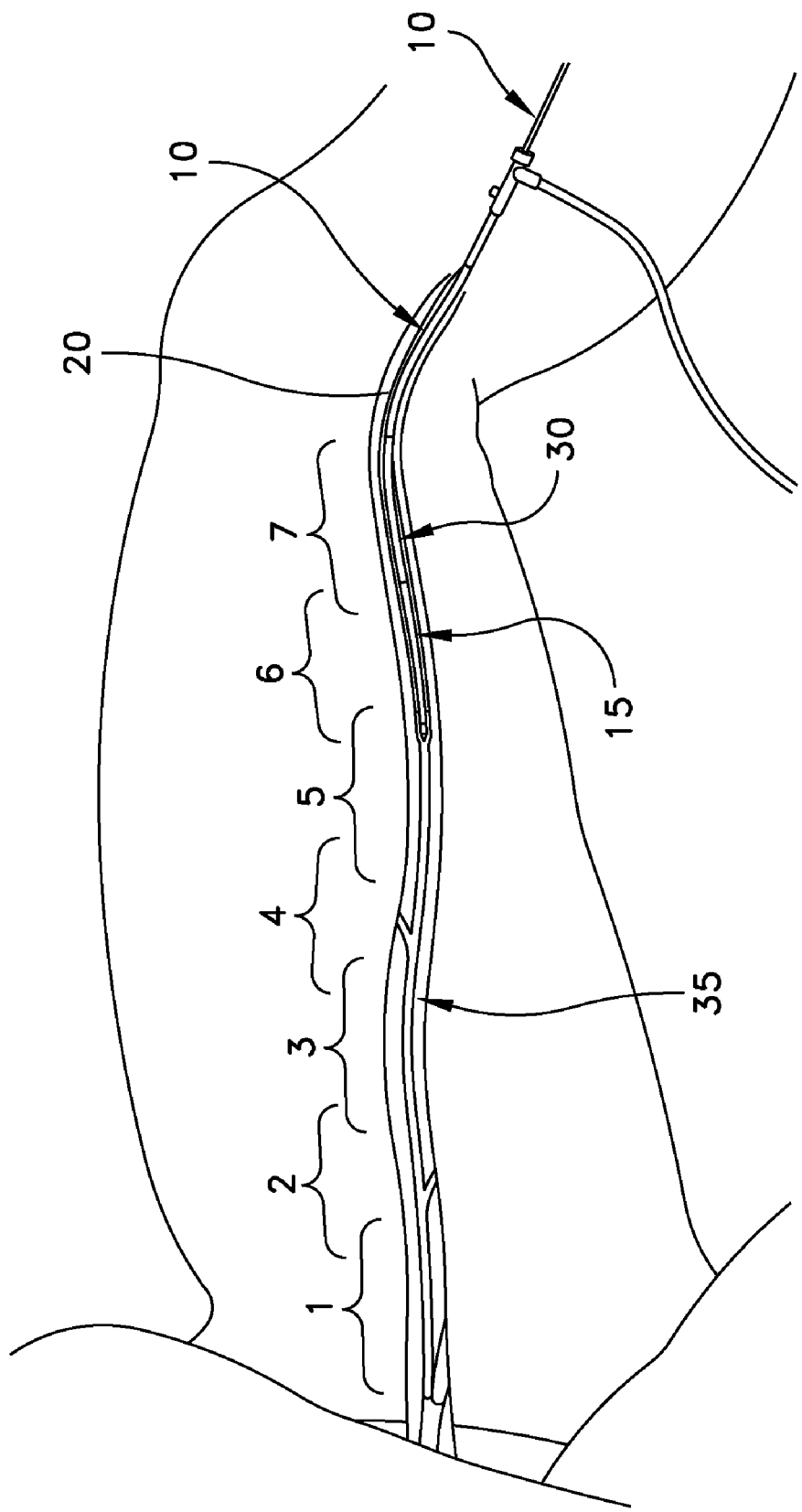
FIG. 3 illustrates seven segments of the vein where the heating coil is maintained during each energy delivery period.
Figure 4:
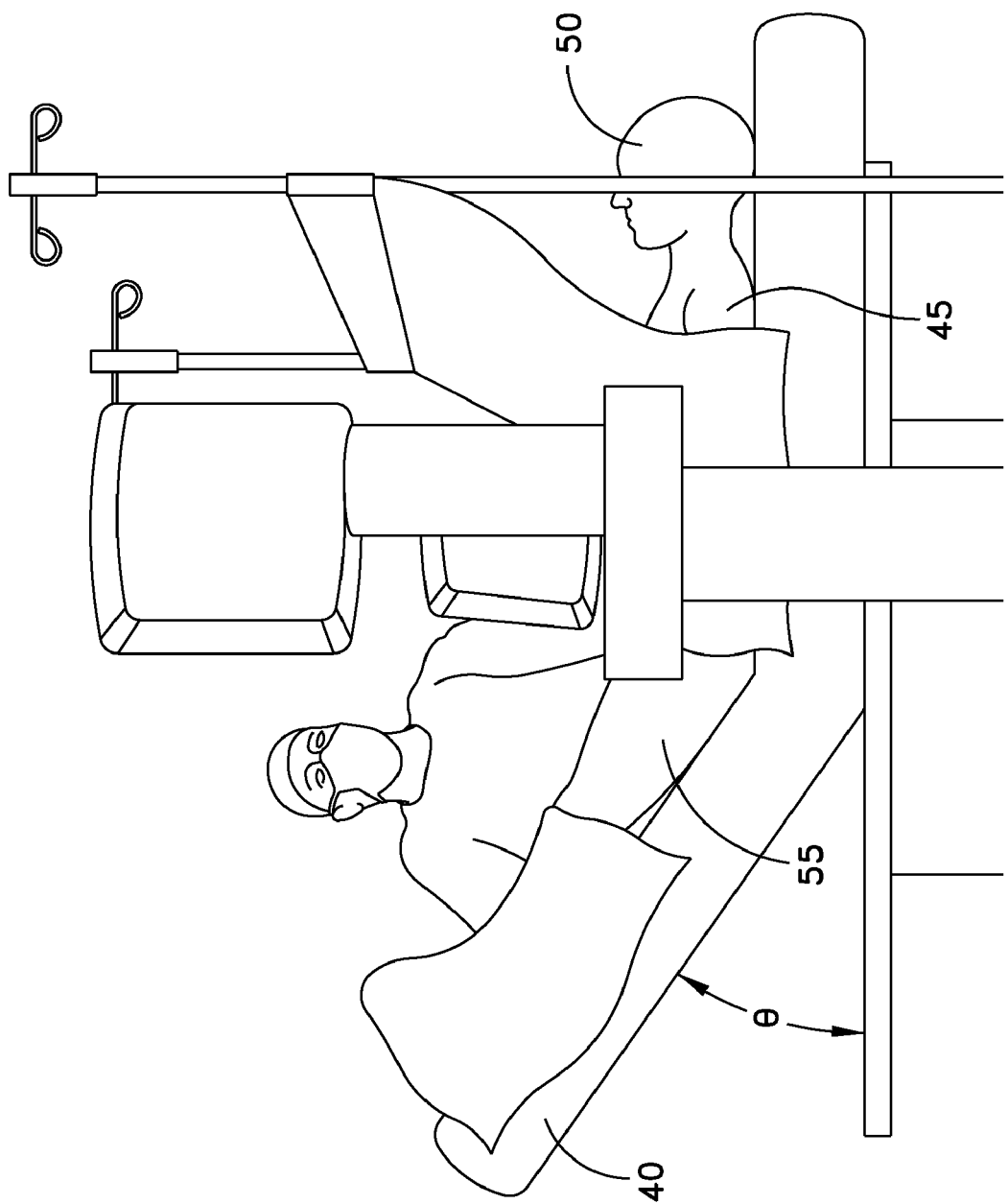
FIG. 4 illustrates the tilt table in this treatment room to allow the torso of the patient to be in a relatively supine position (where patient's head can be seen to the right), while the leg to be treated is positioned with 30° or more of angulation.

In an embodiment, a distal section of a ClosureFAST catheter 10, which contains a 7 cm long heating element 15, is depicted heating the great saphenous vein (GSV) 20 in a segment starting approximately 2 cm below the saphenofemoral junction (SFJ) 25 in FIG. 1. FIG. 2 illustrates the catheter 10 of FIG. 1 prior to heating an open segment 30 of the vein 20 at a heating element 15, with a closed segment 35 of the vein 20 to the left of the open segment 30 to be heated by heating element 15. FIG. 3 illustrates seven segments 1-7 of the vein 20 where the heating coil or element 15 is maintained during each energy delivery period. FIG. 4 illustrates the tilt table 40 in a treatment room allows the torso of the patient to be in a relatively supine position (where patient's head 50 can be seen to the right), while the leg 55 (to be treated) is positioned with 30° or more of angulation θ.

For satisfactory transfer of energy, the electrodes or the element must be in direct contact with the vein wall. The heating causes a physical shortening of the vein wall's collagen fibrils in a mostly uniform manner, primarily in the subendothelial layers. (Manfrini S, Gasbarro V, Danielsson G, et al. Endovenous management of saphenous vein reflux. *J Vasc Surg.* 2000;32:330-42.) A recent report by Schmedt et al corroborates this finding. (Schmedt C G, Meissner O A, Hunger K, et al. Evaluation of endovenous radiofrequency ablation and laser therapy with endoluminal optical coherence tomography in an ex vivo model. *J Vasc Surg.* 2007;45:1047-58.) The vein diameter becomes narrowed while at the same time denatured blood proteins congeal to obliterate the vein lumen. The entire treated vein is affected by this process much like soft boiling an egg. Over the next several months, usually ten to twelve, and certainly by two years, the vein fibroses and is seen to vanish on duplex ultrasound in over 86% of cases. (Pichot O, Kabnick L S, Creton D, et al. Duplex ultrasound scan findings two years after great saphenous vein radiofrequency endovenous obliteration. *J Vasc Surg.* 2004; 39:189-95.) For the ClosurePLUS procedure the process is controlled by a computerized generator (RF1 or RF2) which monitors electrode temperature and adjusts energy levels to achieve a constant heating of the vein wall at a user-selectable temperature, typically 85° or 90°±3° C. During heating, the catheter is withdrawn from the vein typically at a rate of 2-4 centimeters per minute. For the ClosureFAST procedure the newer RF2 generator (which can be used with all VNUS catheters) controls the heating element at 120° C. for a predetermined 20 second period that can be manually interrupted at any moment by the operator.

Major steps of the technique may be practiced as described herein.

Patient anesthesia, is generally a matter between the physician and the patient. However, the procedure itself is well suited for local anesthesia or regional field block such as a femoral nerve block. General anesthesia offers at least one drawback in that the anesthetized patient is unable to communicate nerve pain which might be the result of the heat produced by the catheter coming into proximity with an overlying sensory cutaneous nerve. Minimal sedation with oral (e.g., diazepam) or intravenous (e.g., midazolam and fentanyl) agents is recommended to provide adequate anxiolysis and analgesia. Short acting agents delivered intravenously have been found to offer better control with quick recovery and better patient comfort, thus allowing fast-track post procedure discharge from the facility or office. Midazolam I.V. (of the diazepam family) may offer some protection against lidocaine toxicity.

The catheter may be inserted into the vein at its nearest point to the skin surface, usually just below or above the knee using standard percutaneous (Seldinger) or cut-down technique. The catheter tip is positioned using ultrasound guidance approximately 2 cm distal to the saphenofemoral junction. This is critical to avoid thermal injury to the SFJ. All current Closure devices (VNUS Medical Technologies, San Jose, Calif.) feature a central lumen that will accommodate either a 0.018 (ClosureRFS™) or 0.025 inch (ClosurePLUS™ and ClosureFAST™) diameter guide wire, to allow maneuverability through tortuous or difficult vein segments.

Once the catheter has been positioned safely below the SFJ, tumescent anesthesia can be introduced using a variety of methods. It is important to use ultrasound visualization in order to insure that the fluid is placed beneath the saphenous fascia and above the deep muscular fascia and that it surrounds the vein completely, which serves to contain the radiant heat within the treated vein without significantly affecting adjacent cutaneous and sensory nerve tissues. (Zikorus A W, Mirizzi M S. Evaluation of setpoint temperature and pullback speed on vein adventitial temperature during endovenous radiofrequency energy delivery in an in-vitro model. *Vasc Endovascular Surg.* 2004;38:167-74.) The infusate also compresses the saphenous vein and its inflow branches in order to produce a "dry" vein. Contraction of the vein diameter is another benefit if diluted epinephrine is included in the tumescent anesthetic fluid. Tumescent anesthesia, using generous volumes of buffered lidocaine 1% with epinephrine 1:100,000 diluted to 0.1% placed properly, results in relatively pain free status (see Table 1). Care must be taken to avoid lidocaine toxicity. For example, dosage guidelines are 7 mg/kg body weight, and no more than 500 mg should be used at one setting. Bilateral limb procedures may require alternate anesthesia choice such as general or regional (e.g., femoral nerve block, spinal, or epidural).

Prior to November 2007, during vein heating the patient was positioned in gentle Trendelenburg position, approximately 15-20 degrees. More recently, as depicted in FIG. 2, the patient's head and torso are kept in a relatively comfortable horizontal position while the limb to be treated is elevated at an angle of 30-45 degrees. Ultrasound imaging demonstrates that, while the patient remains comfortable, this extreme position allows for near complete emptying of the venous system with tight circumferential contact of the vein by the catheter. Gentle manual pressure with the diagnostic ultrasound (DUS) probe can be applied to the saphenofemoral junction area and then along the course of the vein as necessary, while the catheter is withdrawn (for ClosurePLUS) or segmentally repositioned (for ClosureFAST).

DUS should be used to document satisfactory closure of the treated vein just before removing the catheter from the vein. When ClosurePLUS is performed, a curious finding on ultrasound that may be observed is echogenic movement depicted in the occluded vein despite having obliterated the lumen. It probably represents movement of saline solution infused through the Closure catheter in the vein and around the blood plug despite adequate obliteration of the lumen. If significant flow remains, the vein should be retreated. When using the ClosureFAST catheter the catheter may not be re-advanced to the SFJ, as doing so may dislodge fibrinous material cephalad into the proximal deep venous system. If there are concerns when treating very large diameter veins, approximately 10 mm or greater, one can simply double heat each 7 cm segment (i.e., two episodes, 20 seconds each) prior to repositioning the catheter. The transfer of heat with ClosureFAST is so uniform and efficient that the vein treated invariably closes when studied postoperatively with DUS.

The patient should be encouraged to ambulate immediately, returning in some cases to normal activities on the same day. Postoperative ultrasound imaging of the saphenofemoral junction within three days is a part of the protocol to check for successful obliteration and absence of clot extension into the common femoral vein. What is usually seen at this initial check is remarkably similar to an acute thrombosis of the vein with dilation and filling of the vein lumen with echo dense signals and failure to compress with externally applied pressure. This represents an element of thrombosis which aids the obliteration process.

Management of Complications

Data collected for the VNUS Closure Study Group Registry was prospective, looking for nerve injury, clot extension, hematoma, phlebitis, skin burns, and infection. (Merchant R F, DePalma R G, Kabnick L S. Endovascular obliteration of saphenous reflux: A multicenter study. *J Vasc Surg.* 2002;35: 1190-6.) Only limbs treated at 85° C. and seen within the first postoperative week were included in the report, and only limbs treated with Closure and ClosurePLUS catheters were included in the Registry. Results are shown in Table 2. The most serious complication, although rare, is clot extension into the common femoral vein as it can lead to deep vein thrombosis (DVT) if not recognized and treated early with either low molecular weight heparin (LMWH) or operative thrombectomy. It is a general practice to see all cases on the first postoperative day and to include a postoperative duplex scan during that visit. If there is evidence of clot extending into the deep vein, then LMWH is prescribed at therapeutic doses for six days. Aspirin 325 mg is started on day 7 and continued for one month.

Nerve injury associated with RF ablation is seen as areas of hypoesthesia noted on follow-up examination in the first week post-op. The majority of these occurred in the early Closure cases before the routine instillation of tumescent anesthesia. To avoid nerve injury, following the early clinical experience, the Closure procedure was recommended to be limited to above knee great saphenous vein (GSV) treatments. (Manfrini S, Gasbarro V, Danielsson G, et al. Endovenous management of saphenous vein reflux. *J Vasc Surg.* 2000;32:330-42.) The greater saphenous nerve is actually adherent to the GSV in the distal leg and injury to this nerve is usually unavoidable when GSV RF ablation is attempted much below the knee. (Chandler J G, Pichot O, Sessa C, et al. Treatment of primary venous insufficiency by endovenous saphenous vein obliteration. *Vasc Surg.* 2000;34: 201-14.)

Skin burns, initially seen in a minority of early Closure cases, essentially have vanished since the institution of tumescent anesthesia (Merchant R F, DePalma R G, Kabnick L S. Endovascular obliteration of saphenous reflux: A multi-center study. *J Vasc Surg.* 2002;35: 1190-6, and Weiss R A, Weiss M A. Controlled radiofrequency endovenous occlusion using a unique radiofrequency catheter under duplex guidance to eliminate saphenous varicose vein reflux: A 2-year follow-up. *Dermatol Surg.* 2002;28:38-42.) and the abandonment of the Eschmark leg wrap. The Eschmark rubber bandage has a tendency to roll back when applied to the funnel shaped thigh, in which case it can act as a tight rubber band to push the skin closer to the saphenous vein. Ablation in the thin or skinny leg should prompt careful attention to detail to minimize thermal injuries to the overlying skin due to excessive external compression, which can arise from the Eschmark bandage or the DUS probe during intraoperative monitoring.

Phlebitis can occur with the Closure procedure as in any treatment of varicose veins, and it is usually the result of residual blood trapped within vein segments. Some degree of phlebitis is inherent in the whole process since the obliteration occurs as a result of injury to the vein by the heating process. It is occasionally seen as a tender, erythematous or ecchymotic band over the treated vein in the distal thigh. It resolves over several weeks without any specific treatment other than for symptomatic relief, e.g. the use of non-steroidal anti-inflammatory drugs, heat, and compression hosiery.

Patients may describe a curious sensation which occurs during the second or third post-op week along the treated vein segment, usually in the distal thigh. They may experience a spontaneous or persistent dull feeling, or "bogginess", or sharpness when stretching or extending the treated leg. This could represent an inflammatory process which occurs as the body is healing the scald injury of the treated vein segment. The sensations usually abate over several weeks, consistent with the normal healing time of injured tissues.

ClosureFAST

The endovenous Closure procedure has evolved from the originally introduced catheter and techniques, to introduction of improved devices (ClosurePLUS, ClosureFAST) and techniques (tumescence) designed to improve outcomes and reduce the incidence of complications, and newly designed devices (ClosureRFS) to broaden applications. The introduction of the ClosureFAST catheter in 2007 was intended to substantially shorten procedure time and it appears that it has done just so. The device has a 7 cm heating element that remains stationary during a 20-second long energy delivery period. The catheter is then repeatedly retracted 6.5 cm and energized for 20 seconds at each segment until the desired length of vein has been treated. The ClosureFAST catheter has undergone successful early clinical studies. Proebstle et al reported on the first multi-center study of 252 GSVs treated in 194 patients. The average energy delivery time was 2.2 minutes over an average 36.7cm vein length; 16.4 minutes average elapsed time from catheter insertion to final removal. Initial vein occlusion was 100% and life-table analysis out to 6 months was 99.6% occlusion rate. (Proebstle T M, Vago B, Alm J, Göckeritz O, Lebard C, Pichot O. Treatment of the incompetent great saphenous vein by endovenous radiofrequency powered segmental thermal ablation: first clinical experience. J Vasc Surg. 2008;47:151-156.) In follow-up, Proebstle reported a 96.7% occlusion rate on 223 vein segments at one year. (Proebstle T M, Vago B, Alm J, Göckeritz O, Lebard C, Pichot O. One year follow-up of radiofrequency segmental thermal ablation (RTFA)-of great saphenous veins. Presented at American Venous Forum 20th annual meeting, Feb. 20-23, 2008; Charleston, S.C.)

The Reno Vein Clinic began using ClosureFAST in May 2007, and by November 2007 had treated 138 saphenous vein segments of which 15 were SSV treatments. Within the first six months, only one segment had completely recanalized, and the complication rates were similar to the ClosurePLUS procedure. However, in several instances there were multiple interruptions of the procedure due to inadequate or uneven heating of the vein segments, which resulted in damage to the heating element portion of six ClosureFAST catheters. In November 2007 an adjustment was made in what proved to be a significant improvement to the technique—the limb undergoing treatment was elevated 30-45 degrees from the horizontal to effect complete emptying of the superficial venous system (see FIG. 2). DUS demonstrated complete emptying of the saphenous vein with tumescence and elevation. Implementation of this maneuver resolved the uneven heating problem, and the average energy delivered to the vein segments dropped from 110 Joules/cm to 60 Joules/cm (average of two procedure measurements). From November 2007 to October 2008 one hundred-thirty-one (131) saphenous vein segments (of which 18 were SSV) were treated with 100% initial occlusion and absence of hypoesthesia and deep venous thrombosis related to the RF procedure. Interruptions ceased and there were no further episodes of heat related catheter damage. One patient suffered a second degree skin burn at the insertion site, probably as a result of inadvertent positioning of the catheter in the introducer sheath during the final segment treatment.

Three key points of the ClosureFAST technique should be emphasized to assure a smooth and successful treatment of the patient:

To avoid possible thermal injury to the SFJ, the catheter tip must be positioned 2 cm distal to the SFJ, regardless of superficial epigastric vein location. One must reaffirm location by longitudinal and transverse DUS images.

There is a step-up hub located 2 cm behind the heating element; use this indicator to locate the position of the catheter beneath the skin at the insertion site during the final segment treatment. This should help avoid skin burns at this location.

Elevate the limb to be treated, either manually or by table reposition, 30-45 degrees during the short two to four minute treatment course. This provides complete emptying of the vein segment and allows a smooth, uninterrupted procedure.

The evidence published in peer reviewed journals, four studies of which are level one, suggests that at least out to five years outcomes of RF obliteration of saphenous vein reflux are comparable to traditional stripping and ligation. The risks of serious complications such as DVT are low and comparable with those that attend stripping and ligation. Lesser complications, when they do occur, are time limited and usually of minor consequence.

Using the RF Closure equipment and employing current techniques described in this report, an experienced clinician, modifying details to suit individual clinical settings, can expect the following: 1) 98-100% successful initial ablation;

2) less than 1% rate of complications such as common femoral vein clot extension and DVT, temporary sensory thermal nerve injury and second degree thermal skin injury; and 3) five-year ablation and reflux-free outcomes of >90%. In high risk patients, e.g. the obese, or those on anticoagulation or having co-morbidities, the Closure procedures may be the better treatment option because of the advantages they offer over traditional surgical methods, especially regarding less trauma. In cases where reflux originates distal to the saphenofemoral junction (which can only be appreciated by DUS), the Closure method is ideally suited.

Neovascularization following this procedure at the saphenofemoral junction appears to only rarely occur and may not be a factor in later recurrent varicose veins, a possible distinct advantage in comparison with surgical stripping and high ligation. (Pichot O, Kabnick L S, Creton D, et al. Duplex ultrasound scan findings two years after great saphenous vein radiofrequency endovenous obliteration. *J Vasc Surg.* 2004; 39:189-95; and Kianifard B, Holdstock J M, Whiteley M S. Radiofrequency ablation (VNUS closure) does not cause neo-vascularisation at the groin at one year: results of a case controlled study. *Surgeon.* 2006;4:71-4.) The persistent patency found in the superficial epigastric vein and other less frequently seen groin branches and the pattern of failures of the Closure procedure have been described recently in the five-year report by the Closure Study Group and the results are encouraging for long term successful relief from superficial venous hypertension and reflux. There is little reason to doubt that results with the new ClosureFAST segmental heating catheter would be any different, if not better; short term reports support this assertion. (Proebstle T M, Vago B, Alm J, Göckeritz O, Lebard C, Pichot O. One year follow-up of radiofrequency segmental thermal ablation (RTFA) of great saphenous veins. Presented at American Venous Forum 20th annual meeting, Feb. 20-23, 2008; Charleston, S.C.)

Radiofrequency obliteration of saphenous vein reflux, given the caveat that it be done by a qualified physician, has become a safe, effective, and preferred alternative to traditional surgical techniques, evidenced by many publications including the Closure Study Group five-year outcomes. Schmedt et al, reporting certain anatomical findings by an innovative research investigational tool, endoluminal optical coherence tomography (eOCT), demonstrated a more uniform and complete disintegration of the radiofrequency (ClosurePLUS, 6Fr) treated bovine vein compared to endovenous laser treated bovine vein. (Schmedt C G, Meissner O A, Hunger K, et al. Evaluation of endovenous radiofrequency ablation and laser therapy with endoluminal optical coherence tomography in an ex vivo model. J Vasc Surg. 2007;45: 1047-58.) Whether radiofrequency deserves to be the treatment of choice among endovenous obliteration procedures will require further well designed randomized studies. In the meantime it makes sense to offer this innovative technology as a primary choice for the patient with saphenous vein reflux of primary origin.

TABLE 1

| Tumescent anesthesia solution preparation | |
|---|---|
| Ringer's Lactate | 500 cc |
| Withdraw 50 cc | −50 cc |
| | 450 cc |
| Add lidocaine 1% with epinephrine 1:100,000 | +50 cc |
| | 500 cc |

TABLE 1-continued

| Tumescent anesthesia solution preparation | |
|---|---|
| Add sodium bicarbonate (NaHCO$_3$) 8.4% | +16 cc |
| Resultant solution is lidocaine 0.1% with epinephrine 1:1 million | 516 cc |

TABLE 2

Complications reported from the Closure Study Group

| Complication | Follow-up interval | Rate of occurrence, % (n/N) |
|---|---|---|
| DVT (accompanied by pulmonary embolism in one instance) | One week | 1.0 (3/286) |
| Skin burn - first half of study | One week | 4.2 (6/143) |
| Skin burn - second half of study | One week | 0 (0/143) |
| Infection | One week | 0 (0/286) |
| Clinical phlebitis | One week | 2.1 (6/286) |
| Clinical phlebitis | Six months | 0.4 (1/223) |
| Paresthesia | One week | 15.0 (43/286) |
| Paresthesia | Six months | 9.4 (21/223) |
| Paresthesia | 12 months | 3.9 (9/232) |
| Paresthesia | 24 months | 5.6 (8/142) |

What is claimed is:

1. A method of closing a vein within a leg of a patient, the vein closing method comprising:
   A. elevating the leg of the patient during a vein closure procedure at least 30 degrees above a horizontal position; and
   B. heating within a predetermined portion of the vein within the leg of the patient during the vein closure procedure;
   whereby the predetermined portion of the vein within the leg of the patient closes.

2. A vein closure method in accordance with claim 1, wherein heating of step (B) occurs while the leg of the patient is elevated in step (A).

3. A vein closure method in accordance with claim 2, further comprising, during the heating step (B), applying radio-frequency (RF) energy to a heating coil of a catheter within the vein within the leg of the patient.

4. A vein closure method in accordance with claim 3, further comprising during the radio-frequency (RF) energy applying step, applying light pressure toward the heating coil of the catheter.

5. A vein closure method in accordance with claim 3, further comprising positioning a distal end of the catheter about 2 cm distal from the saphenofemoral junction.

6. A vein closure method in accordance with claim 5, wherein the positioning of the distal end of the catheter occurs without regard to superficial epigastric vein location.

7. A vein closure method in accordance with claim 5, further comprising using a step-up hub located about 2 cm behind the heating coil and locating the catheter beneath the skin at an intersection site during a final segment treatment.

8. A vein closure method in accordance with claim 3, further comprising, during the leg elevating step (A), emptying of a predetermined segment of the vein of the patient prior to, during the heating step (B), applying the radio-frequency (RF) energy within the predetermined segment of the vein of the leg of the patient.

9. A vein closure method in accordance with claim 8, further comprising, during vein segment emptying, providing tight circumferential contact of the vein of the leg of the patient by catheter simulations.

10. A vein closure method in accordance with claim 8, further comprising introducing tumescent anesthesia to the patient.

11. A vein closure method in accordance with claim 10, further comprising, during the radio-frequency (RF) energy applying step, maintaining the heating coil stationary during a radio-frequency (RF) energy applying period.

12. A vein closure method in accordance to claim 11, wherein the radio-frequency (RF) energy applying period is 20 seconds.

13. A vein closure method in accordance to claim 11, wherein the catheter is retracted 6.5 cm after the radio-frequency (RF) energy applying period.

14. A vein closure method in accordance with claim 3, further comprising maintaining the heating coil stationary during the radio-frequency (RF) energy applying step.

15. A vein closure method in accordance with claim 1, further comprising completing the vein closure procedure for the leg in a period of time of less than 2 minutes from an initial application of heat to the vein within the leg of the patient during the heat applying step (B).

16. A vein closure method in accordance with claim 1, further comprising using a step-up hub located about 2 cm behind the heating coil and locating the catheter beneath the skin at an intersection site during a final segment treatment.

17. A method of closing a vein segment within a leg of a patient, the vein segment closure method comprising:
   A. elevating the leg of the patient during a vein closure procedure within a range of substantially above 30 degrees to about 45 degrees from a horizontal position; and
   B. applying radio-frequency (RF) energy within the vein segment within the leg of the patient to cause the vein segment to close within the leg of the patient elevated within the range of substantially above 30 degrees to about 45 degrees.

18. A method of closing a vein segment within a leg of a patient, the vein segment closure method comprising:
   A. elevating the leg of a patient during a vein closure procedure to at least 30 degrees above a horizontal leg position;
   B. while maintaining the leg elevating of step A, emptying of the vein segment prior to applying energy adjacent the vein segment; and
   C. while maintaining the leg elevating of step A, applying the energy adjacent the vein segment within the leg of the patient to cause vein closure.

19. A method of vein closure according to claim 18 further comprising, while maintaining the leg elevating of step (A), maintaining the patient's back at a horizontal patient back position.

20. A vein closure method in accordance to claim 19, wherein the energy is provided by a laser.

21. A vein closure method in accordance to claim 19, wherein the energy is provided by steam.

22. A vein closure method in accordance to claim 19, wherein the energy is electromagnetic energy.

* * * * *